United States Patent
Diaz et al.

(10) Patent No.: US 9,949,779 B2
(45) Date of Patent: Apr. 24, 2018

(54) TRANSOSSEOUS RIBBON WIRE DEVICES AND A SYSTEM AND METHOD FOR USING THE DEVICES

(71) Applicant: RMD Enterprises Group LLC, Miami, FL (US)

(72) Inventors: Rosendo Miguel Diaz, Miami, FL (US); Gregorio Caban, Miami Gardens, FL (US); Mario Adrian Cala, Miami, FL (US)

(73) Assignee: RMD ENTERPRISES GROUP LLC, Miami, FL (US)

( * ) Notice: Subject to any disclaimer, the term of this patent is extended or adjusted under 35 U.S.C. 154(b) by 0 days.

(21) Appl. No.: 14/866,263

(22) Filed: Sep. 25, 2015

(65) Prior Publication Data

US 2016/0089194 A1    Mar. 31, 2016

Related U.S. Application Data

(60) Provisional application No. 62/056,173, filed on Sep. 26, 2014.

(51) Int. Cl.

| A61B 17/88 | (2006.01) |
|---|---|
| A61B 17/16 | (2006.01) |
| A61B 17/84 | (2006.01) |
| A61B 17/60 | (2006.01) |
| A61B 17/62 | (2006.01) |
| A61B 17/64 | (2006.01) |
| A61B 17/56 | (2006.01) |

(52) U.S. Cl.
CPC .......... *A61B 17/8861* (2013.01); *A61B 17/16* (2013.01); *A61B 17/848* (2013.01); *A61B 17/8872* (2013.01); *A61B 17/8897* (2013.01); *A61B 17/60* (2013.01); *A61B 17/62* (2013.01); *A61B 17/6458* (2013.01); *A61B 2017/564* (2013.01)

(58) Field of Classification Search
CPC . A61B 17/8861; A61B 17/8872; A61B 17/62; A61B 17/8869
See application file for complete search history.

(56) References Cited

U.S. PATENT DOCUMENTS

| 7,780,444 B1 | 8/2010 | Schendel | |
|---|---|---|---|
| 2003/0009217 A1* | 1/2003 | McKernan | A61B 17/1714 623/13.14 |
| 2006/0189992 A1 | 8/2006 | Medoff | |
| 2006/0272730 A1* | 12/2006 | de Oliveira | A61B 17/8869 140/123.6 |
| 2006/0276809 A1* | 12/2006 | de Oliveira | A61B 17/06 606/151 |

(Continued)

OTHER PUBLICATIONS

Dec. 22, 2015: International Search Report and Written Opinion for PCT/US2015/052327.

*Primary Examiner* — Julianna N Harvey
(74) *Attorney, Agent, or Firm* — Heslin Rothenberg Farley & Mesiti P.C.; Jacquelyn A. Graff

(57) ABSTRACT

Devices for use in performing external fixation orthopedic surgery are provided. More particularly, a specialized transosseous wire having a rectangular cross-section is provided. The specialized wire is installed using a reciprocating motion. Thereafter, the specialized transosseous wires are affixed to a frame. Methods of using the transosseous wire are also disclosed.

14 Claims, 5 Drawing Sheets

(56) References Cited

U.S. PATENT DOCUMENTS

| | | | |
|---|---|---|---|
| 2008/0188859 A1* | 8/2008 | Reitzig | A61B 17/8861 |
| | | | 606/103 |
| 2010/0137923 A1 | 6/2010 | Greenhalgh et al. | |
| 2011/0034925 A1 | 2/2011 | Tipirneni et al. | |
| 2016/0256194 A1* | 9/2016 | Wong | A61B 17/171 |

* cited by examiner

FIG. 1
PRIOR ART
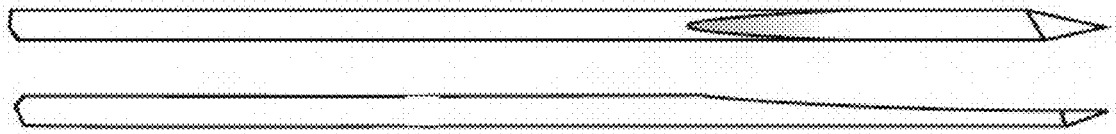
FIG. 2
PRIOR ART
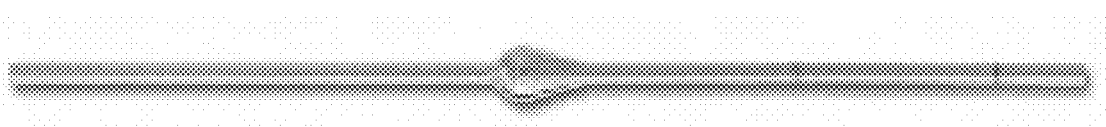
FIG. 3
PRIOR ART
FIG. 4
PRIOR ART
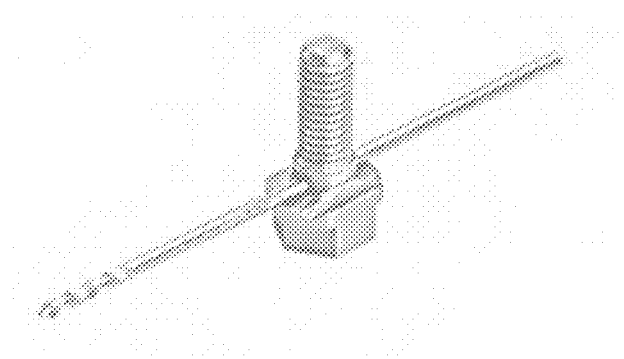
FIG. 5
PRIOR ART

TRANSOSSEOUS RIBBON WIRE DEVICES AND A SYSTEM AND METHOD FOR USING THE DEVICES

CROSS REFERENCE TO RELATED APPLICATION

This application claims priority benefit under 35 U.S.C. § 119(e) of U.S. provisional application No. 62/056,173 filed Sep. 26, 2014, which is incorporated herein by reference in its entirety.

BACKGROUND OF THE INVENTION

Field of the Invention

The invention relates to the area of external fixation devices used in orthopedic surgery and, more particularly to specialized transosseous wires and assemblies for use with an external fixator.

Description of the Related Art

External fixators for correcting bone malunions, non-unions, acute fractures, deformities and defects are known. For example, external fixation has been performed since the 1950's to lengthen bones and correct deformities using an "Ilizarov" apparatus. The Ilizarov apparatus uses circular rings and semi-circular external supports centered on a patient's limb and secured to the bone by crossed, tensioned wires and half pins.

Such system use wires, pins and half-pins traditionally having a circular cross-section. FIGS. 1-3 show prior art wires and FIG. 4 shows a prior art half pin presently used in Ilizarov assemblies (as shown more particularly in FIG. 4). Such prior art wires and half pins are characterized by a circular cross-section in the wire portion remaining in the bone. However, such circular wires can, in some circumstances, tear out of soft or degraded bone when tension or loads are applied. What is needed is an implant that is fixed to the ring external fixation device at two points having a surface area that will not readily tear out or cut through soft bone.

What is needed is a system and method utilizing an external fixator wherein transosseous wires are provided with a non-circular cross-section and mounted to external hardware having a mating cross-section. What is additionally needed is a method for installing a transosseous wire having more surface area through the use of a non-circular cross-section.

BRIEF SUMMARY OF THE INVENTION

It is accordingly an object of this invention to provide a transosseous ribbon wire and hardware, and a system and method for performing external fixation in orthopedic surgery that overcome the disadvantages of the prior art. In one particular embodiment of the invention, a specialized transosseous wire having a rectangular cross-section is provided. In another embodiment, the specialized wire is installed using a reciprocating motion. Thereafter, the specialized transosseous wires are affixed to an external fixation frame.

In one aspect, provided herein is a transosseous wire device, including a ribbon wire and a delivery tool.

In another aspect, provided herein is a method of implanting a transosseous wire, including providing a transosseous wire with a rectangular cross-section, placing the wire in a delivery tool, and advancing the wire through a bone using a reciprocating motion.

In yet another aspect, provided herein is a method of using a transosseous wire device, including providing a transosseous wire having a rectangular cross-section in a body portion of the transosseous wire for a length sufficient to traverse a bone, the transosseous wire including a cutting tip at a first end of the wire. The method further includes placing the wire in the sheath of a delivery tool, with the cutting tip of the wire disposed proximal to an opening in the channel at the distal end of the sheath. The delivery tool includes a sheath with a first end and a second end, a handle at the first end, an opening at the second end, a cavity extending from the second end of the sheath to the handle, a slot extending along a length of the sheath from an exterior surface of the sheath into the cavity, a driver with a hole and a tang end positioned opposite the hole in the driver and shaped to couple to a reciprocating saw, and a pin coupled to the driver through the hole and coupled to the connector hole of the ribbon wire at a first end. The method further includes engaging one end of the pin to the connector hole of the transosseous wire, the other end of the pin being engaged with the driver, connecting the tang end of the driver to a reciprocating saw, and operating the reciprocating saw to advance the transosseous wire into, and through, a bone.

In another aspect, provided herein is a fastener for securing a transosseous wire to an external fixator, including a threaded portion and a rectangular-shaped portion configured to receive a wire having a rectangular cross-section.

Although the invention is illustrated and described herein as embodied in transosseous ribbon wires, hardware and devices for performing external fixation and a system and method of using the devices, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a top plan view of a prior art wire having a circular cross-section and a bayonet shaped, eccentric tip for drilling through bone, which is used in performing external fixation in an Ilizarov procedure;

FIG. 2 is a side plan view of the prior art wire of FIG. 1;

FIG. 3 is a top plan view of a prior art beaded or stopper wire having a circular cross-section, which is used in performing external fixation in an Ilizarov procedure;

FIG. 4 is a top plan view of a prior art half pin having a circular cross-section, which is used in performing external fixation in an Ilizarov procedure;

FIG. 5 is a partial perspective view of a prior art wire fixation bolt used to capture a prior art wire having a circular cross-section in an Ilizarov procedure;

DETAILED DESCRIPTION OF THE INVENTION

Figure 6:
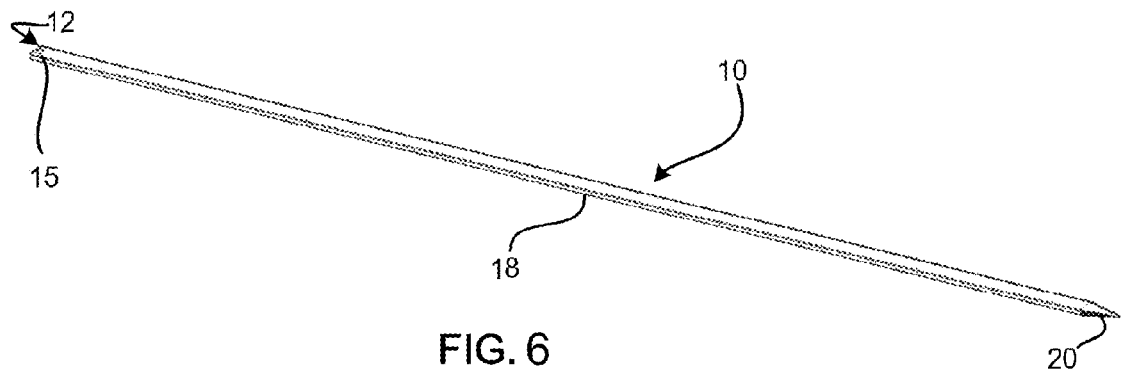
FIG. 6 is a perspective view of a smooth transosseous ribbon wire, in accordance with an embodiment of the present disclosure.
Figure 7:
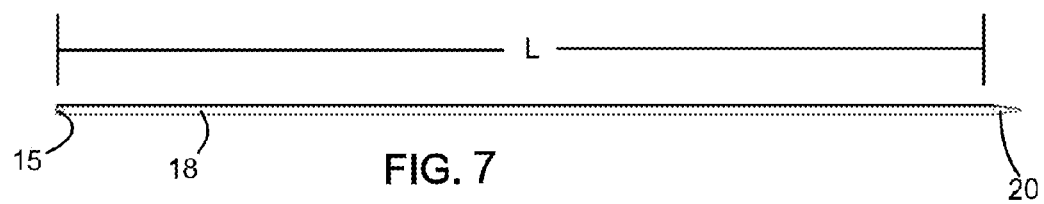
FIG. 7 is a side plan view of the transosseous ribbon wire of FIG. 6, in accordance with an embodiment of the present disclosure.
Figure 8:
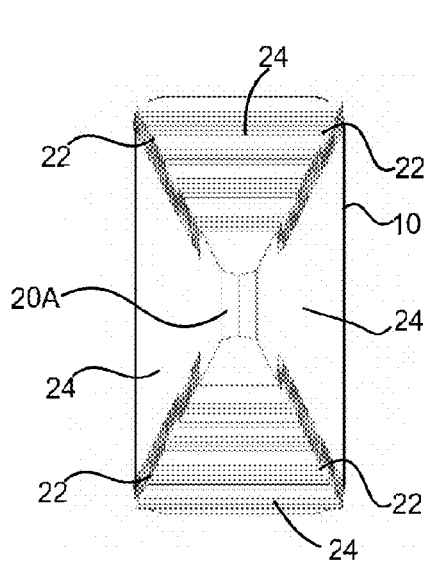
FIG. 8 is a front end plan view of the smooth transosseous ribbon wire of FIG. 6, in accordance with an embodiment of the present disclosure.
Figure 9:
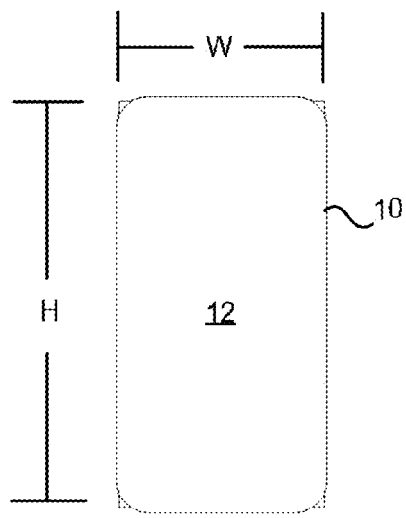
FIG. 9 is a rear end plan view of the smooth transosseous ribbon wire of FIG. 6, in accordance with an embodiment of the present disclosure.

Generally stated, disclosed herein are transosseous ribbon wire devices. Further, a system and method for using the transosseous ribbon wire devices is also discussed.

Referring now to FIGS. 6-9, there will now be described a transosseous ribbon wire 10 which may be used in performing external fixation, such as an Ilizarov fixation, in accordance with an embodiment of the present disclosure. More particularly, a transosseous wire is provided in the form of a ribbon or bar 10, such that it has a rectangular cross-section. The terms "transosseous ribbon wire", "ribbon wire", "wire", "ribbon", "transosseous ribbon fastener", "ribbon fastener", "fastener", "transosseous ribbon implant", "ribbon implant", "implant", "transosseous bar", and "bar" may be used interchangeably herein to describe the same device. In one embodiment, the transosseous ribbon wire 10 is a rectangular prism, having a height "H" that is greater than the width "W". In another embodiment, the height "H" is, for example, about twice the width "W". In yet another embodiment, the height "H" is, for example, three times or more the width "W". In a further embodiment, for example, the width "W" of the ribbon wire 10 is, for example, approximately 1.5-2.5 mm, while the height "H" is selected to be in a range from, and including, approximately 3-8 mm. In one embodiment, the width "W" is, for example, 1.8 mm and the height "H" is, for example, 4 mm. In another embodiment, the width "W" is, for example, 1.8 mm and the height "H" is, for example, 6 mm. In a further embodiment, the width "W" of the ribbon wire 10 is, for example, 2.0 mm and the height "H" is, for example, 6 mm. This is not meant to be limiting, as other dimensions suitable for use in external fixation of bone can be used without departing from the scope or spirit of the invention.

In accordance with one embodiment, the ribbon wire 10 is rectangular along the majority of the length "L" (i.e., along the longitudinal axis of the ribbon wire 10). A boring tip 20 may be provided at one end of the ribbon wire 10, for use in sawing into the bone through which the wire 10 is to be inserted. The boring tip 20 may have, for example, a pyramidal shape, with each side 22 converging on a sharpened cutting blade 20A. The tip 20 may be, for example, ridged, and/or the edges can be sharpened, to enhance cutting into the bone. Alternately, the faces 24 of the tip 20 can be, for example, curved (preferably, concave) or fluted to assist in moving the bone out of the hole being cut. Additionally, the ribbon wire 10 can be made from a bio-compatible material, for example, titanium, stainless steel, or the like. Such material should be chosen to have sufficient strength and rigidity to permit the wire 10 to be sawed into the bone, in accordance with a method described in further detail below.

The ribbon wire 10 may also include a body 18 extending between the boring tip 20 and a second end 12 of the ribbon wire 10. The second end 12 may be positioned opposite the boring tip 20. The ribbon wire 10 may also include at least one engagement or connector hole 15 near the second end 12 of the ribbon wire 10. The hole 15 is used to engage the ribbon wire 10 with a delivery tool, as will be described in greater detail below. In one embodiment, the hole 15 is shaped to be non-circular, for example, square, rectangular, hexagonal, octagonal, or another polygonal shape, so as to engage the tool without permitting the tool to rotate in the hole 15. The hole 15 is hexagonal in the illustrated embodiments.

Figure 10:
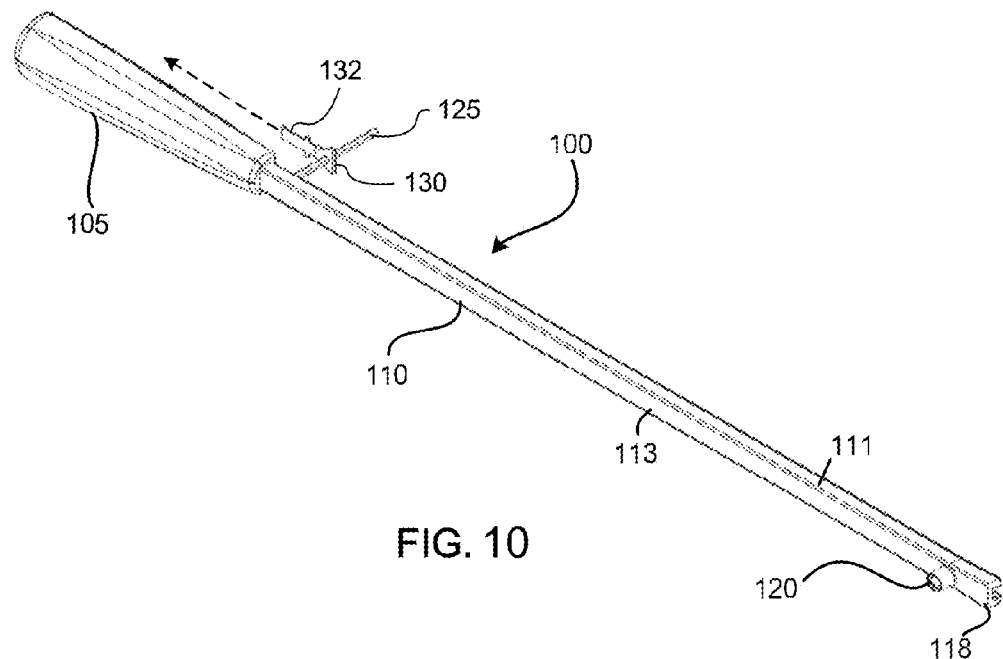
FIG. 10 is a first side perspective view of a delivery tool and ribbon wire system, in accordance with an embodiment of the present disclosure.
Figure 11:
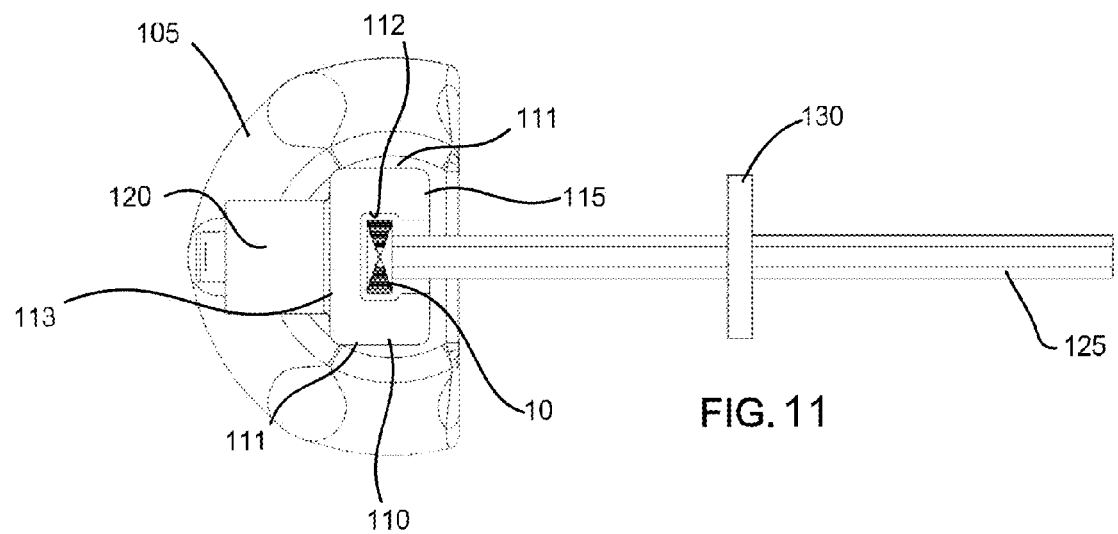
FIG. 11 is an enlarged, front plan view of the delivery tool and ribbon wire system of FIG. 10, in accordance with an embodiment of the present disclosure.

Referring now to FIGS. 10-14, there is shown an embodiment of a delivery tool 100, for inserting the ribbon wire 10 through a bone, in accordance with one embodiment. More particularly, the delivery tool 100 can be used with the wire 10 for installing the wire 10 into and through the bone when performing an Ilizarov type or other orthopedic procedure. The delivery tool 100 may include a handle portion 105 engaged with a ribbon sheath 110. The ribbon sheath 110 may be hollow and may include an inner channel or cavity 112, as shown in FIG. 11. The cavity 112 may preferably have a rectangular cross-section complementary to that of the ribbon wire 10. The ribbon sheath 110 may also have a roughly "C" shaped cross-section defined by opposing upper and lower walls and, by a solid side wall 113, opposite a slotted side wall 115, as shown in FIG. 11. Ribbon wire 10 is slidably received within the slot 112 of the ribbon sheath 110 through an orifice at the end 118 of the ribbon sheath 110. The end 118 of the ribbon sheath 110 may include a rocker tip at the point of contact with the patient.

Figure 12:
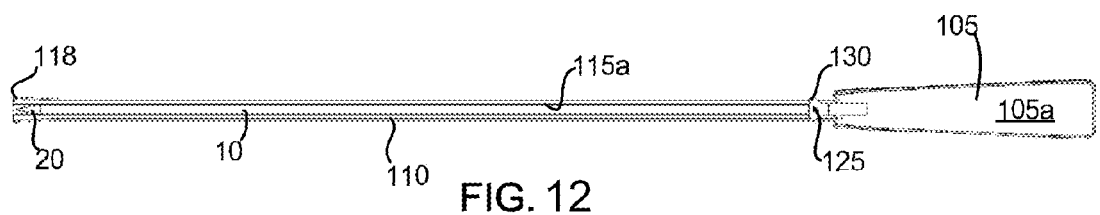
FIG. 12 is a side plan view of the delivery tool and ribbon wire system of FIG. 10, in accordance with an embodiment of the present disclosure.
Figure 13:
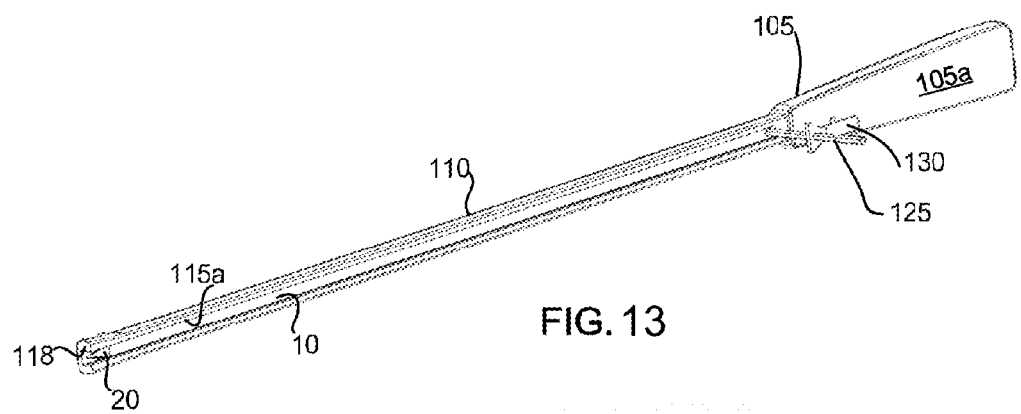
FIG. 13 is a second side perspective view of the delivery tool and ribbon wire system of FIG. 10, taken from the side opposite the first side, in accordance with an embodiment of the present disclosure.
Figure 14:
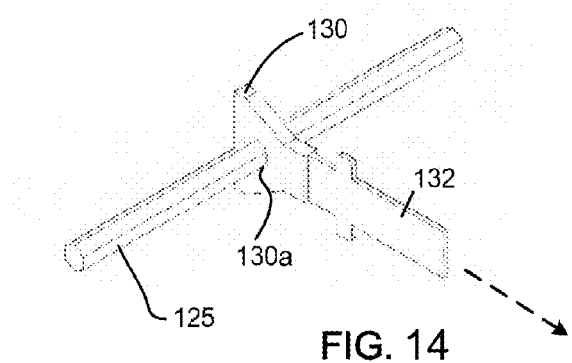
FIG. 14 is an enlarged, perspective view of a driver assembly useful with a delivery tool and ribbon wire system of an embodiment of the present disclosure.

Referring now to FIGS. 12-14, the slotted side wall 115 of the ribbon sheath 110 includes a slot 115a, through which the hole 15 of the ribbon wire 10 can be accessed. The delivery tool 100 may also include a pin 125, which may be passed through the slot 115a to engage the hole 15 in order to facilitate the sliding of the ribbon wire 10 within and outside of the sheath 110, as shown in FIGS. 11-13. The delivery tool 100 may also include a driver 130 with a hole 130a at a first end and a tang end 132 at a second end of the driver 130. The hole 130a of the driver 130 may receive the pin 125. In the embodiment shown in FIG. 14, the pin 125 has a non-circular cross-sectional shape, for example, a hexagonal shape, that is complementary to the cross-sectional shapes of the holes 15 and 130a, to prevent unwanted rotation of the rod 125. The tang end 132 of the driver 130 may be configured to be received into the blade clamp holder or shoe of a reciprocating saw (not shown). When engaged with a reciprocating saw or other power attachment, the driver 130 drives the travel of the ribbon wire 10 from inside of the sheath 110 into, and through, a bone of the patient.

The delivery tool 100 may additionally include a Luer lock connector 120 on the side 113 of the sheath 110, as shown in FIG. 10. The lock connector 120 may be in fluid communication with the cavity 112 of the ribbon shaft 110, so as to provide saline or water into the cavity 112 during the procedure, to cool the ribbon wire 10 during insertion and prevent heat induced osteonecrosis. In one embodiment, the Luer lock connector 120 is placed one (1) inch from the distal end 118 of the ribbon sheath 110.

Referring now to FIGS. 6-14, there will be described a method for assembling a delivery system with a ribbon wire, in accordance with one embodiment. More particularly, the method may include loading a ribbon wire 10 into the sheath 110 of the delivery tool 100. The ribbon wire 10 may have a rectangular cross-section through the length "L" of its body 18, as described in greater detail above. Next, the pin 125 of the driver 130 may optionally be attached to the ribbon wire 10 before loading into the tool 100, to assist in loading the ribbon wire 10. The pin 125 may be attached to the ribbon wire 10 by inserting the pin 125 into the hole 15 in the second end 12 of the ribbon wire 10. The pin 125 may optionally be coupled to the driver 130 prior to or after insertion of the pin 125 into the hole 15 of the ribbon wire 10. Once the pin 125 is coupled to the ribbon wire 10, the ribbon wire 10 may be inserted into the slot 115a at the end 118 of the delivery tool 100. The ribbon wire 10 may be slid through the slot 115a until the ribbon wire 10 is seated in the cavity 112. The ribbon wire 10 may be seated in the cavity 112 with the end 12 of the ribbon wire 10 at the handle 105 or at a desired position along the cavity 112. After the ribbon wire 10 is fully inserted into the delivery tool 100 and the pin 125 and driver 130 assembled, the tang end 132 of the driver may be coupled to a reciprocating saw, as indicated by the arrows in FIGS. 10 and 14.

In an alternative method of assembly, the ribbon wire 10 may be inserted into the sheath 110 of the delivery tool 100 prior to coupling the pin 125. The ribbon wire 10 may be seated in a position with the end 12 of the ribbon wire 10 at the handle 105 or at a desired position along the cavity 112. In this embodiment, after the ribbon wire 10 is seated in the cavity 112, the pin 125 may be inserted into the hole 15 of the ribbon wire 10. The pin 125 may be coupled to the driver 130 prior to or after insertion of the pin 125 into the hole 15 of the ribbon wire 10. After the ribbon wire 10 is fully inserted into the delivery tool 100 and the pin 125 and driver 130 assembled, the tang end 132 of the driver may be coupled to a reciprocating saw, as indicated by the arrows in FIGS. 10 and 14.

Figure 19:
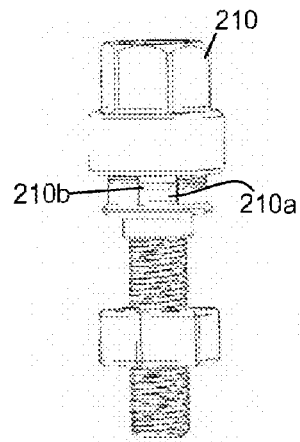
FIG. 19 is a front plan view of a transosseous ribbon implant fixation bolt and set screw, in accordance with another embodiment of the present disclosure.
Figure 20:
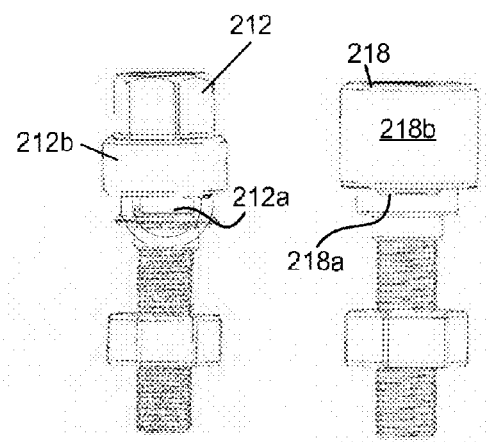
FIG. 20 is a front plan view of a transosseous ribbon implant fixation bolt, in accordance with a further embodiment of the present disclosure.

Referring now to FIGS. 6-21, there will be described a method for using a ribbon wire and delivery system in accordance with one embodiment. The method may include, for example, a surgeon positioning and attaching a frame 200 around the patient's bone needing fixation. Next, a trajectory guide, for example, a guide 212 as shown in FIG. 20, may optionally be attached to the frame 200 in a desired position to assist with insertion of a ribbon wire 10. Once the surgeon has determined the insertion position for the ribbon wire 10 to enter the patient's body, a stab incision may be made using a small surgical scalpel blade. The stab incision will allow the sheath 110 to enter the patient's body and serve as a soft tissue protector as well as a guide for the implant. Next, the surgeon may obtain the delivery tool 100 and ribbon wire 10 for insertion into the patient. In one embodiment, the delivery tool 100 will be provided to a physician pre-assembled, as shown in FIG. 10. In an alternative embodiment, the delivery tool 100 and ribbon wire 10 may be provided un-assembled and would need to be assembled during the surgery.

Once the delivery tool 100 and ribbon wire 10 are assembled, the ribbon wire 10 will be fully received into the cavity 112 and the tang end 132 of the driver 130 will be locked into the shoe of a reciprocating saw. The surgeon may then hold the handle 105 of the sheath 110 in one hand, and the reciprocating saw body in the other hand. In the embodiment illustrated, the handle 105 has a flattened face 105a that will be near, or in contact with, the body of the reciprocating saw. Holding the handle in one hand, the tool 100 is disposed adjacent to the entry position for the ribbon wire. The distal end 118 of the delivery tool 100 may be, for example, placed on the patient's skin at the point of the stab incision or, if a trajectory guide is being used, the distal end 118 may be placed with the ribbon wire 10 adjacent to the opening in the trajectory guide 212. Next, with the reciprocating saw turned on, the surgeon may advance the saw and the ribbon wire 10 (via the driver 130 and pin 125), such that the cutting tip of the ribbon wire 10 emerges from the distal end 118 of the sheath 110. The reciprocating motion of the ribbon wire (imparted by the saw via the driver 130 and pin 125) causes the blade tip 20a of the ribbon wire 10 to cut into the soft tissue and bone of the patient. The surgeon continues to advance the saw, while holding the handle 105 steady in the original position, until the ribbon wire 10 traverses the soft tissue and bone of the patient and emerges from the other side. The tool 100 and pin 125 can then be disconnected from the ribbon wire 10, with the ribbon wire 10 still traversing the bone.

The ribbon wire 10 can then be attached at a first end to an external fixator ring 200 using a bolt or other attachment mechanism, for example, bolt 210, 212, 214, 218. If a trajectory guide was used, then the trajectory guide may be removed and replaced by a bolt 210, 212, 214, 218 or other attachment mechanism on the first end. Next, another bolt 210, 212, 214, 218 or attachment mechanism may be used to secure the ribbon wire 10 on a second end. Optionally, a tensioner (not shown) may be used to apply tension to the ribbon wire 10 before securing the ribbon wire 10 to the frame 200 with a second bolt 210, 212, 214, 218, as described in greater detail below. Use of the tensioner (not shown) enables the surgeon to secure the ribbon wire 10 in tension. Once the ribbon wire 10 is secured to the frame 200 on each end, the excess ribbon wire 10 may be removed from each end.

The method may further include pre-drilling an opening into the patient's bone prior to inserting the ribbon wire 10. The pre-drilling may be used when the ribbon wire 10 is being inserted through a long, dense cortical bone. The opening that is drilled in the patient's bone may be, for example, smaller than the size of the ribbon wire 10. The opening may be, for example, smaller than 2 mm, such as 1.5 to 1.8 mm.

It should be understood that other forms of ribbon wires can be used without departing from the scope and spirit of the present invention. For example, referring now to FIGS. 15 and 16, the principles of the present disclosure can be applied to other types of transosseous wire, such as stopper wire 150. As with the embodiment of FIG. 10, the stopper wire 150 has a body portion 152 having a rectangular cross-section, sized and dimensioned as described in connection with ribbon wire 10 which will not be described again here for brevity sake, including a boring tip 158 and an engagement hole 154 for connection to a drive rod. However, the ribbon wire 150 also includes a stopper portion 156 to provide a stop at the bone interface.

A delivery tool 160, similar in all respects to delivery tool 100, as described in greater detail above and which will not be described again here for brevity sake. The delivery tool 160 may include a cavity 165 of the sheath 162 that has been sized or otherwise configured to receive the ribbon wire 150, including its larger stopper 156. Additionally, the orifice at the distal end 168 of the sheath 160 would be sized and configured to permit the stopper 156 to exit therefrom.

The foregoing disclosure provides an improved transosseous wire, system and method for use in external fixation surgery. By providing a transosseous wire having a greater surface area, the present disclosure provides an increased pullout resistance for the wire and greater load bearing properties. An insertion tool is provided for installing the inventive ribbon wire through the bone. Additionally, the present disclosure provides improved hardware for securing the ribbon wire to an external fixator, such as a ring fixator or other type of external frame. More particularly, referring now to FIG. 17, there is shown one embodiment of external fixator hardware 200 for performing external fixation surgery using the ribbon wires 10, 150, described herein. More particularly, the hardware 200 is used to maintain tensioned ribbon wires 10 using fasteners 210, 212, 214 to secure the wires 10 to the frame or hardware 200.

Figure 18:
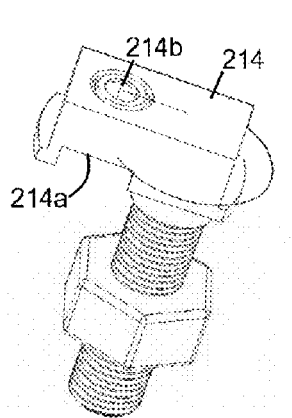
FIG. 18 is a perspective view of an off center transosseous ribbon fixation bolt and set screw, in accordance with an embodiment of the present disclosure.
Figure 21:
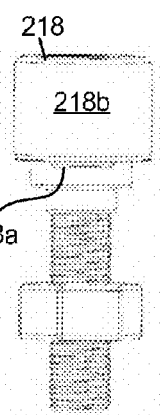
FIG. 21 is a front plan view of a bolt, in accordance with yet another embodiment of the present disclosure.
Figure 15:
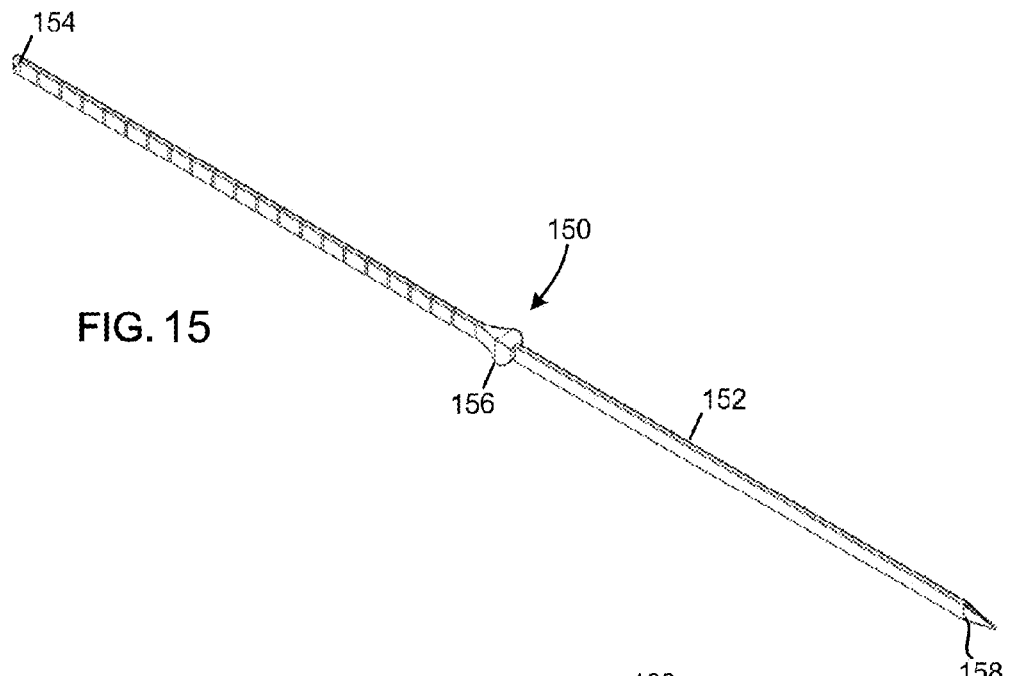
FIG. 15 is a perspective view of a transosseous stopper ribbon wire, in accordance with an embodiment of the present disclosure.
Figure 16:
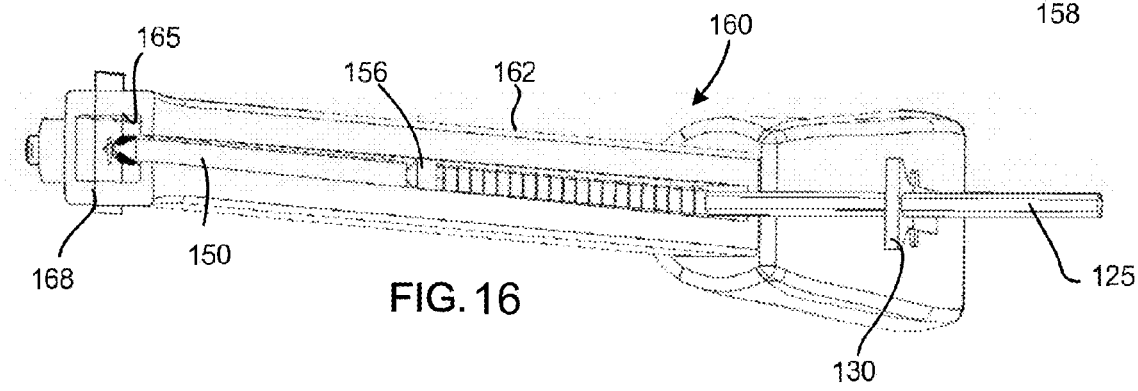
FIG. 16 is a perspective view of a delivery tool and ribbon wire system, in accordance with another embodiment of the present disclosure.
Figure 17:
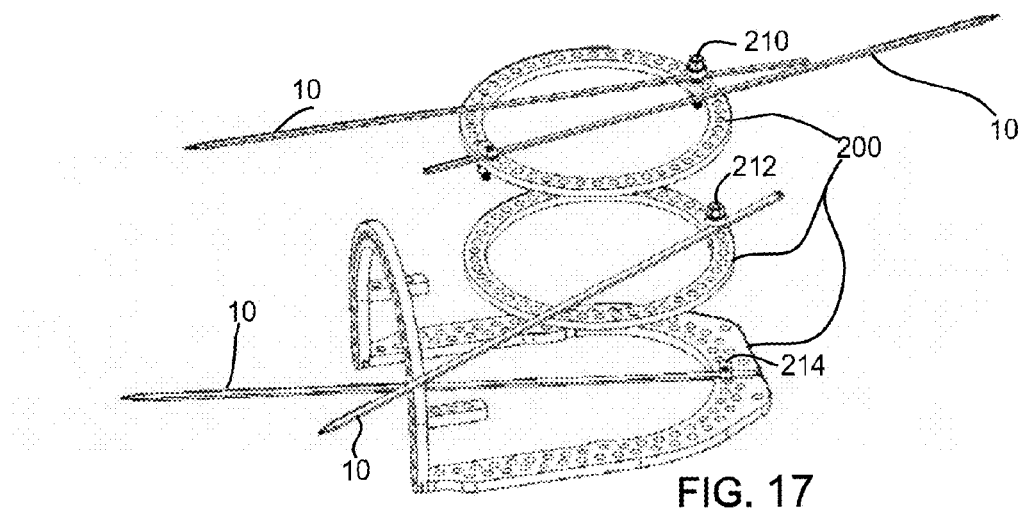
FIG. 17 is a perspective view of an external fixator using transosseous ribbon wires, in accordance with an embodiment of the present disclosure.

More particularly, external fixation can be performed using ribbon wires 10, 150, as described herein, wherein the ribbon wires 10, 150 are secured to the hardware 200 using traditional fasteners. However, in one embodiment, specialized fasteners 210, 212, 214 having portions adapted to fit the rectangular cross-sections of the wires 10, 150 are provided. Referring now to FIGS. 18-20, there are shown fasteners 210, 212, 214, that can be used with the wires 10, 150 having a rectangular cross-section. As shown, each of the fasteners 210, 212, 214 includes a rectangular cavity 210a, 212a, 214a, for receiving and tightly holding the rectangular bodies of the wires 10, 150. Additionally, the off-center bolt 214 includes a set screw 214b, which can be used to tighten the wire 10, 150 firmly against the hardware 200, using a hex wrench. Similarly, the fastener 210 includes a protrusion 210b that can be used to firmly trap the wire in the rectangular cavity 210a. The fastener 212 includes a mechanism wherein the cap 212b is tightened down on the body of the wire 10, 150 to hold it in place. Other fasteners can be used to engage a wire having a rectangular cross-section without departing from the scope and spirit of the present disclosure. For example, FIG. 21 shows another type of fastener 218 including a rectangular cavity 218a and a biased cap 218b which is biased to move the cap downwards, for example, toward the threaded shank of the bolt, to entrap and retain the ribbon wire 10, 150 tightly in the cavity 218a through friction.

It is also contemplated that the ribbon wire 10, 150 may be tensioned in accordance with the requirements of an Ilizarov procedure. Tensioning of the ribbon wire 10, 150 involves drawing the wire against its fixed end. Wire tensioners are known, such as the TRUELOK™ wire tensioner, in which the tensioner is slid over the wire to be tensioned, while the head captures the wire fixation bolt and is firmly against the external support. The TRUELOK™ wire tensioner operates by squeezing the handles of that tool together until the desired amount of tension is generated in the wire. Note that such a wire tensioner can be adapted specifically to work with (i.e., fit over and accept) ribbon wires 10, 150 of various diameters, as described herein. Additionally, in one embodiment, the wire tensioner includes a set device or temporary, resettable locking device that allows for the wire tensioner to be reset on the same wire for additional tension, if required, without losing the tension gained from the last use. In one particular embodiment, the temporary locking device is a collet that is set when tensioning the transosseous wire or ribbon wire 10, 150, and, after releasing the grip, can be reset to add additional tension to the same wire.

Although described herein with an external fixator such as the Ilizarov fixator, it should be understood that the transosseous ribbon wire of the present disclosure could also be used as a standalone bone fixation and stabilization implant due to its shape and method of insertion, without departing from the scope and spirit of the present disclosure.

Accordingly, while a preferred embodiment of the present disclosure is shown and described herein, it will be understood that the invention may be embodied otherwise than as herein specifically illustrated or described, and that within the embodiments certain changes in the detail and construction, as well as the arrangement of the parts, may be made without departing from the principles of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention claimed is:

1. A transosseous wire device, comprising:
a ribbon wire; and
a delivery tool; and
wherein the ribbon wire comprises:
a body with a first end and a second end;
a boring tip at the first end, wherein the boring tip is configured for boring into bone; and
a connector hole at the second end for coupling to the delivery tool; and
wherein the delivery tool comprises:
a sheath with a first end and a second end;

a handle at the first end;
an opening at the second end;
a cavity extending from the second end of the sheath to the handle;
a slot extending along a length of the sheath from an exterior surface of the sheath into the cavity;
a driver with a hole and a tang end positioned opposite the hole in the driver and shaped to couple to a reciprocating saw; and
a pin coupled to the driver through the hole and coupled to the connector hole of the ribbon wire at the first end; and
wherein the tang end is rectangular and includes a top surface opposite a bottom surface, the tang end further comprising:
a first projection extending perpendicular from the top surface; and
a second projection extending perpendicular from the bottom surface; and
wherein the tang end is received within the reciprocating saw and is configured to move with the reciprocating saw.

2. The device of claim 1, wherein the body has a rectangular cross-section between the boring tip and the connector hole for a length sufficient to traverse a bone.

3. The device of claim 1, wherein the boring tip is configured as a pyramidal shape.

4. The device of claim 1, wherein the body includes a stopper positioned between the first end and the second end and wherein the stopper extends in two perpendicular directions relative to a longitudinal axis of the body.

5. The device of claim 1, wherein the delivery tool further comprises:
a lock connector coupled to the sheath on a side opposite the slot.

6. The device of claim 1, wherein the ribbon wire is positioned within the cavity.

7. The device of claim 1, wherein the sheath comprises:
an internal chamber dimensioned to receive the ribbon wire therein and at least one sidewall including a slot through at least a portion of the length of the sidewall;
wherein the pin is disposed through the slot and the ribbon wire is disposed in the internal chamber; and
wherein the driver engages a portion of the pin extending outside the sheath and the tang end is configured to engage a shoe of the reciprocating saw.

8. The device of claim 7, wherein the opening is at an end of the sheath distal from the handle.

9. The device of claim 8, wherein the connector hole of the ribbon wire has a non-circular cross-section and the pin has a corresponding cross-section relative to the connector hole.

10. The device of claim 9, wherein the driver includes a hole for receiving the pin and the hole has a non-circular cross-section corresponding to the shape of the hole of the ribbon wire.

11. A method of implanting a transosseous wire, comprising:
providing a transosseous wire with a rectangular cross-section, wherein the transosseous wire comprises:
a body with a first end and a second end;
a boring tip at the first end, wherein the boring tip is configured for boring into bone; and
a connector hole at the second end for coupling to a delivery tool;
placing the wire in the delivery tool, wherein the delivery tool comprises:
a sheath with a first end and a second end;
a handle at the first end;
an opening at the second end;
a cavity extending from the second end of the sheath to the handle;
a slot extending along a length of the sheath from an exterior surface of the sheath into the cavity;
a driver with a hole and a tang end positioned opposite the hole in the driver and shaped to couple to a reciprocating saw; and
a pin coupled to the driver through the hole and coupled to the connector hole of the ribbon wire at the first end; and
wherein the tang end is rectangular and includes a top surface opposite a bottom surface, the tang end further comprising:
a first projection extending perpendicular from the top surface; and
a second projection extending perpendicular from the bottom surface; and
wherein the tang end is received within the reciprocating saw and is configured to move with the reciprocating saw; and
advancing the wire through a bone using a reciprocating motion.

12. The method of claim 11, wherein the body includes a stopper positioned between the first end and the second end and wherein the stopper extends out from the body in two perpendicular directions relative to the longitudinal axis of the body.

13. The method of claim 11, wherein the rectangular cross-section extends between the boring tip and the connector hole a defined a length sufficient to traverse a bone, and wherein the boring tip has a pyramidal shape.

14. A method of using a transosseous wire device, comprising:
providing a transosseous wire having a rectangular cross-section in a body portion of the transosseous wire for transversing a bone, the transosseous wire has a cutting tip at a first end of the wire that is configured for boring into bone and a connector hole at a second end for coupling to a delivery tool, wherein the delivery tool comprises:
a sheath with a first end and a second end, wherein the sheath comprises:
an internal chamber dimensioned to receive the ribbon wire therein and at least one sidewall including a slot through at least a portion of the length of the sidewalk;
a handle at the first end;
an opening at the second end;
a cavity extending from the second end of the sheath to the handle;
a slot extending along a length of the sheath from an exterior surface of the sheath into the cavity;
a driver with a hole and a tang end positioned opposite the hole in the driver and shaped to couple to a reciprocating saw; and
a pin coupled to the driver through the hole and coupled to the connector hole of the ribbon wire at the first end; and
wherein the tang end is rectangular and includes a top surface opposite a bottom surface, the tang end further comprising:
a first projection extending perpendicular from the top surface; and a second projection extending perpendicular from the bottom surface; and wherein the tang end is received within the reciprocating saw and is configured to move with the reciprocating saw;

placing the wire in the sheath of the delivery tool with the pin disposed through the slot, the ribbon wire disposed in the internal chamber, the driver engaging a portion of the pin extending outside the sheath, the tang end configured to engage a shoe of the reciprocating saw, and the cutting tip of the wire disposed proximal to an opening in the channel at the distal end of the sheath;

engaging one end of the pin to the connector hole of the transosseous wire, the other end of the pin being coupled to the driver;

connecting the tang end of the driver to a reciprocating saw; and operating the reciprocating saw to advance the transosseous wire into, and through, a bone.

* * * * *